United States Patent [19]

Bauer

[11] Patent Number: 4,689,047
[45] Date of Patent: Aug. 25, 1987

[54] AIR VENTING WINGED CATHETER UNIT

[76] Inventor: Gary W. Bauer, P.O. Box 2092, Dayton, Ohio 45429

[21] Appl. No.: 832,362

[22] Filed: Feb. 24, 1986

[51] Int. Cl.$^4$ ............................................. A61M 5/00
[52] U.S. Cl. .................................. 604/122; 604/169; 604/248
[58] Field of Search ................ 604/122, 125, 164–169, 604/179–180, 248, 249

[56] References Cited

U.S. PATENT DOCUMENTS

| | | | |
|---|---|---|---|
| 1,944,553 | 1/1934 | Freund | 604/249 |
| 3,630,195 | 12/1971 | Santomieri | 604/180 X |
| 3,774,604 | 11/1973 | Danielson | 604/169 |
| 4,016,879 | 4/1977 | Mellor | 604/169 X |
| 4,311,137 | 1/1982 | Gerard | 604/122 X |
| 4,540,411 | 9/1985 | Bodicky | 604/169 |

Primary Examiner—Dalton L. Truluck
Attorney, Agent, or Firm—Malin, Haley & McHale

[57] ABSTRACT

This disclosure is directed to an improved winged catheter unit characterized by a combination of beneficial and advantageous features enabling the user to introduce intravenous (I.V.) fluids into a patient while permitting the technician to control air venting at the onset of the I.V. introduction and during change of I.V. bottles without removal of the catheter while at the same time promoting a higher confidence level of avoidance of air embolism(s). This combination also reduces the number of venipunctures necessary to secure placement and maintenance of the needle and catheter tubing. This improved winged catheter unit is characterized by a combination comprising an integral molded deck unit having centrally located therein a tapered tubular inlet portion having a larger inner diameter opening at one end through which an I.V. needle is inserted and a smaller tapered tubular outlet portion through which said needle exits to communicate with a cannula tube surrounding said needle, a rotary or slide valve communicating within said tapered tubular portion between said tapered inlet and outlet, means to position said valve between venting and fluid flow positions while substantially avoiding air entrapment, a catheter inlet closure means adaptable for direct needle insertion of medication without additional venipuncture and at least one integral tube clip portion located on said catheter deck unit.

10 Claims, 9 Drawing Figures

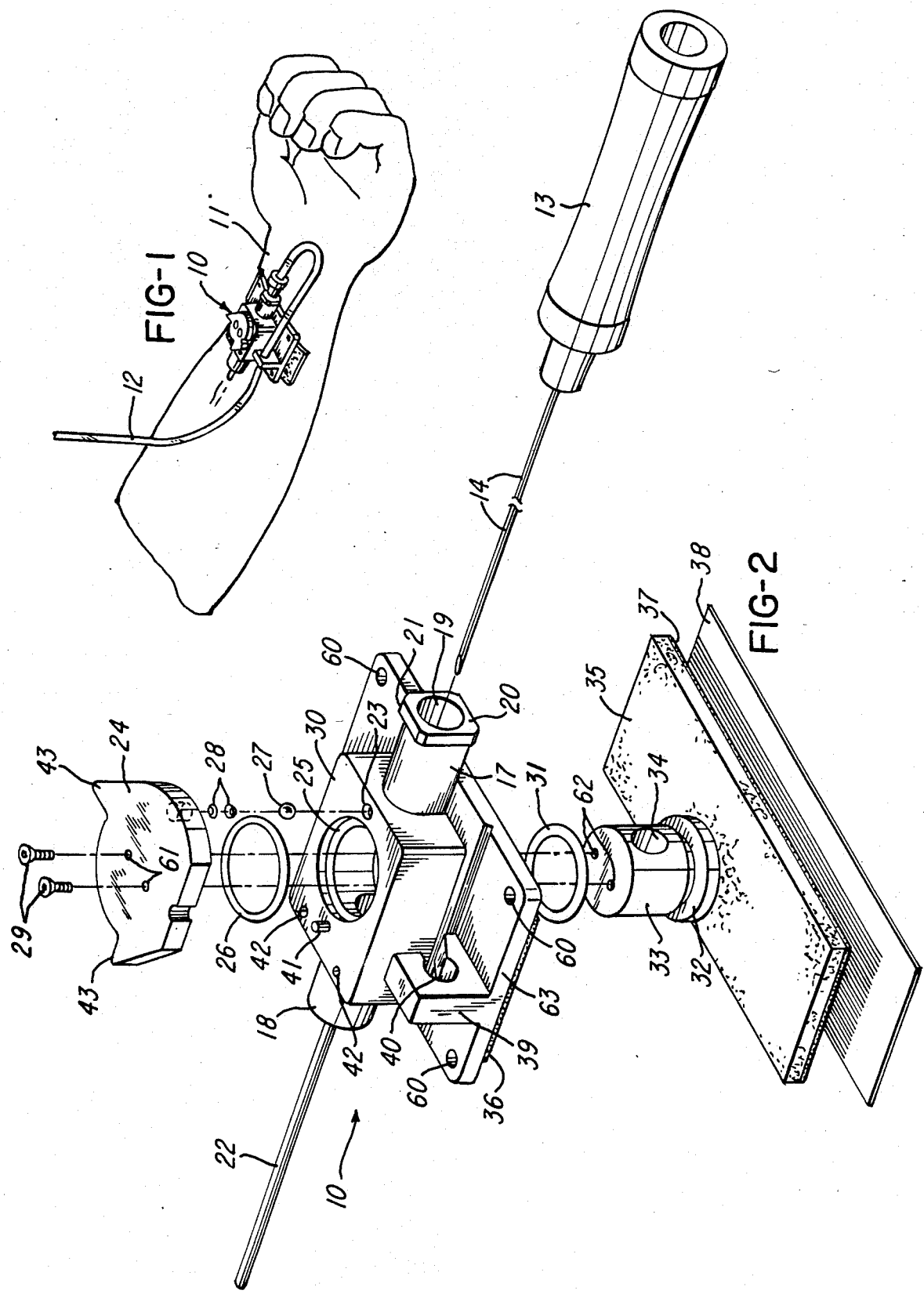

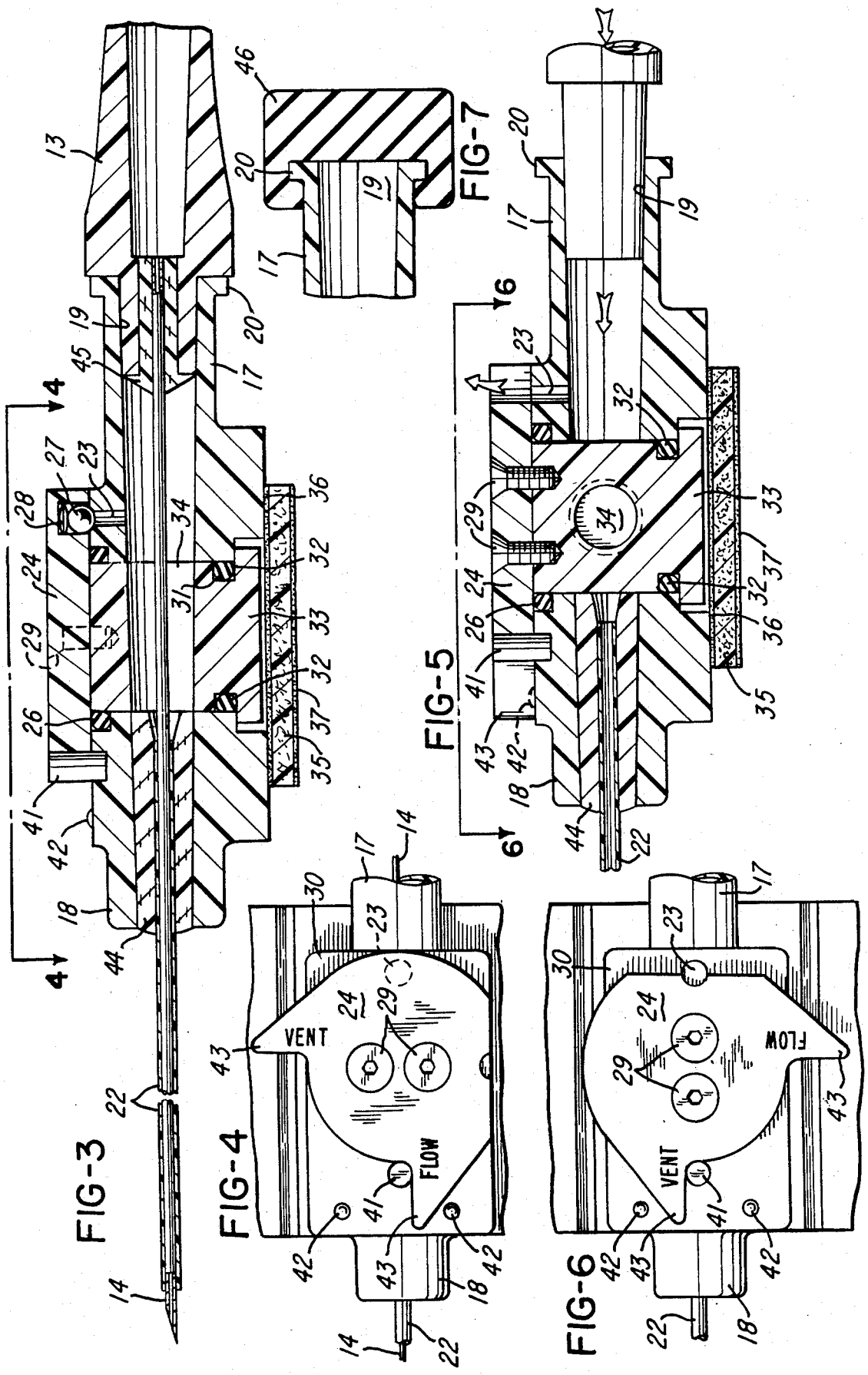

4,689,047

AIR VENTING WINGED CATHETER UNIT

The present invention is directed to an improved winged catheter having a safety-controllable intravenous (I.V.) fluid injection means with improved features permitting controlled air venting and alternate fluid flow and allowing change of I.V. bottles while the catheter is fixed in position on the patient. These improved features are comprised of an integral molded deck unit having centrally located therein a tapered tubular inlet portion having a larger inner diameter opening at one end through which an I.V. needle is inserted and a smaller tapered tubular outlet portion through which said needle exits to communicate with a cannula tube surrounding said needle, a rotary or slide valve communicating within said tapered tubular portion between said tapered inlet and outlet, means to position said valve between venting and fluid flow positions while substantially avoiding air entrapment, a catheter inlet closure means for direct needle insertion of medication without additional venipuncture and at least one integral tube clip portion located on said catheter deck unit.

BACKGROUND OF THE INVENTION AND PRIOR ART

In the emergency transportation of patients from an area at which they become ill to a primary treatment source, such as a hospital, time is frequently of the essence. Although the art of transport of such emergency victims and patients has progressed to the state where many communities have paramedics and paramedical-type vehicles manned by trained technicians and equipped for communication with the hospital to which the patient is being transported, frequently the necessity to quickly transport the patient means that the patient is being given fluids by means of a catheter with needed medications during transport.

This can present a very difficult situation for the paramedic or technician who is inserting the catheter and hazards to the patient not the least of which is the risk of introducing an air embolism into the venous and/or arterial system of the patient, which can be fatal. Under such circumstances of transport, it is customary for the paramedic or technician to receive instructions as to what I.V. material(s) the patient is to be given based on the communication of vital signs and changes in vital signs, such as blood pressure, temperature, pulse, respiration, etc.

Similarly it is not unusual under these circumstances for difficulty to be encountered in inserting the catheter needle during venipuncture, and frequently several or more such venipuncture attempts are required before satisfactory venipuncture is obtained while the technician is doing his best to avoid introducing air into the patient's veins. Not only do these activities present difficulties with regard to the handling of the patient, but it is intimidating to the technician during the transport.

After inserting the cannula and removing the stylet (needle), the tubing leading from the I.V. bottle is coupled to the catheter. It is during this coupling that potential air can be trapped in the tubing and when the clamp is released on the tubing, air can be pushed by the incoming fluids forcing the air in the tubing to enter the patient. A potential fatal embolus could then occur. The device of this invention allows this trapped air to be vented in the catheter reducing the risk of air embolism.

Various solutions to the foregoing problems have been proposed in varying ways in different patents. For example, U.S. Pat. No. 4,417,886 issued to Paul L. Frankhouser, et al. contains a guide tube extending rearwardly from the hub on the back of the catheter needle. A wire guide is mounted in the tube with a wire guide actuating handle projecting through an elongated slot in the side wall of the tubing. The introducer assembly for such catheter is contained in a sterile package and removed as an entire unit including needle, catheter, wire guide and wire guide feed device. Such catheter introduction set is intended for use in placing I.V. lines into small vessels such as the radial artery of a patient. The wire guide has a handle which is adapted to advance a spring wire guide through the lumen of the needle and outwardly from the distal end into and through the lumen of the blood vessel into which the I.V. line is being placed.

U.S. Pat. No. 4,389,210, issued to Joseph N. Genese, includes a spliced two-part needle and a catheter unit comprising a catheter, winged catheter insertion means, flexible tubing and a tube hub, wherein axial and rotational alignment of the needle and catheter unit are maintained by mechanically interlocked complimentary portions of the needle and lumen of the winged catheter insertion means. After venipuncture has been achieved and the catheter has been fully inserted into the vein, the wings are then taped to the patient in accordance with the conventional techniques for so doing.

U.S. Pat. No. 4,193,399, issued to Thomas P. Robinson, discloses a self-venting plug for a venous entry unit which is a porous plastic body adapted to be removably seated in a hollow flashback chamber. The plug comprises an open pored plastic having a pore size on the order of 10 to 15 microns, and provides a flow path for venting air from the flashback chamber while inhibiting flow of blood from the chamber. The plug may be used, for example, with over-the-needle and through-the-needle catheter units employing piercing needles, and may be used to anchor a stylet for stiffening a catheter to be forwarded into the body.

U.S. Pat. No. 3,714,945, issued to Vayden F. Stanley, is directed to an over-the-needle catheter insertion device wherein the catheter and needle are connected to respective interconnecting hub members. The catheter hub member is connectable to an infusion source for an I.V. fluid. The catheter hub member has an outwardly extending ridge molded integrally therewith, providing a means by which the catheter hub and needle hub can be separated by manipulation by only one hand. This separating means is disclosed as being operable by digit flexure of the operator's thumb leaving the technician's other hand free to apply pressure in the area of the venipuncture in order to prevent blood flow through the catheter. Alternatively, the thumb or thumbnail can engage the rearward portion or bib of the catheter hub to remove the needle hub and the needle.

U.S. Pat. No. 3,721,231, issued to Franz Hans Hubert, is directed to a medical catheter formed from a hub from within which an elongated flexible tube is disposed. The bore of the tubing within the hub is tapered to accept the tapered tip of a male connector. The tubing is coextensive with the shaft of the hub. There is also disclosed a method for fabricating the catheter involving mounting the hub on a mandrel which has a tapered portion, adapted to be positioned within the hub, and an elongated pilot extending from the tapered portion through the hub. Heat softenable catheter tubing is fed onto the tapered portion until resistance is met, then the tubing while heat softened, is forced over the tapered portion of the mandrel in the recess between the tapered portion and the hub. The tubing is solidified and the joined catheter removed from the mandrel. The Hubert invention is directed to a medical catheter particularly suitable for high pressure applications, such as high pressure angiocardiography injection machines where an internal pressure in the order of 1,100 pounds per square inch is developed within the hub and the catheter.

U.S. Pat. No. 3,589,361, issued to Douglas A. Loper, is directed to an intravenous catheter, of the needle-inside type, having a wing assembly serving to guide the catheter and needle during venipuncture and adapted to hold the catheter firmly in place after venipuncture. The design of the Loper catheter wings enables the technician to grasp the wings during venipuncture permitting use of the wings to guide the needle and thus the I.V. tubing passing there through. The bottom portion of the wings can have pressure sensitive adhesive applied directly thereto in order to adhesively attach the catheter to the patient's body thereby holding it in place.

It will be observed that the improved winged catheter device of the present invention has several advantages over that of Loper. According to the present invention, the structure of the wing portions of the catheter is such that an air breathing foam lies intermediate between the flexible plastic wings and the pressure sensitive adhesive which is in contact with the patient's skin. A release layer, which can be paper or plastic material, is in contact with the adhesive and upon removal thereof the adhesive then contacts the patient's skin for immobilization of the position of the catheter after venipuncture and placement of the I.V. tubing have been obtained. Moreover, in accordance with one embodiment of this invention, the central housing portion of the catheter unit has molded integrally therewith a grooved or slotted wing portion for holding the I.V. tubing in place. Alternatively, one or both of the I.V. wings can have clips or other tubing-retaining members molded on the supper surface(s) thereof to provide for positioning of the I.V. tubing between its intravenous position and the I.V. bag or bottle from which the intravenous fluid is administered to the patient.

BRIEF DESCRIPTION OF THE DRAWINGS

FIG. 1 of the drawings is a fragmentary perspective view of the gas-venting winged catheter unit of this invention in place on a patient's wrist to show environment of use.

FIG. 2 is an exploded perspective view on a much enlarged scale to show components in greater detail.

FIG. 3 is a fragmentary cross-sectional view of the catheter of this invention in the fluid flow and insertable position and serves to further illustrate the detail of the bottom portion of the catheter unit from an anterior (front) to posterior (rear) position.

FIG. 4 is a top plan fragmentary view taken along line 4—4 of FIG. 3.

FIG. 5 is a fragmentary cross-sectional view of FIG. 3 showing the catheter unit in the vent or fluid shut-off (no I.V. fluid flow) position enabling a medial portion of the I.V. line to be secured on the upper surface of the catheter unit in the immediate vicinity of the venipuncture.

FIG. 6 is a top plan view taken substantially along line 6—6 of FIG. 5.

FIG. 9 is a view similar to that of FIG. 8, but illustrating another modification of the catheter unit utilizing side mounted flow/venting valve means including a spring means which is mounted in a direction generally parallel to that of the catheter portion to which line 12 is attached.

DETAILED DESCRIPTION OF THE INVENTION

Figure 7:
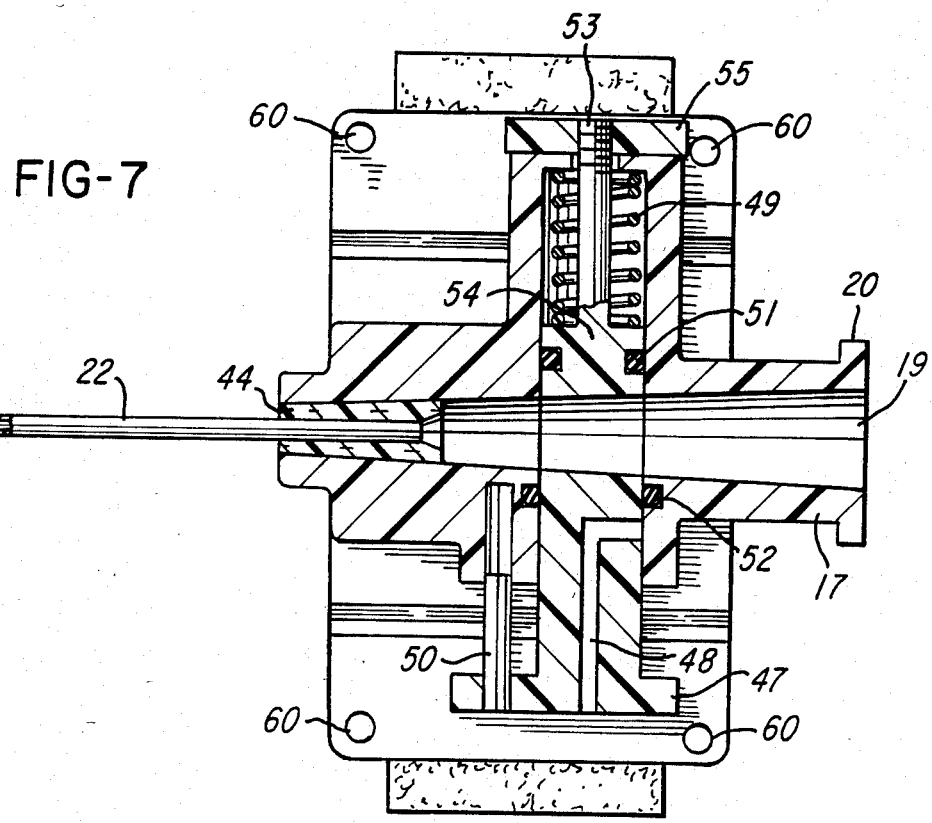
FIG. 7 is a fragmentary cross-sectional view showing the closure (cap) means for the catheter unit.

As will be observed from FIG. 1, catheter unit 10 is shown in place on the lower surface (planar) 11 of the patient's wrist. I.V. feed bottle flow tube (line) 12 is shown held in position by catheter unit curved receptacle portion 40 to retain the line 12 in position during administration of intravenous (I.V.) liquids to the patient.

As will be shown from the right hand lower portion of FIG. 2, needle body 13 has located at one end a hollow needle 14 which is bonded to the needle body and is inserted through the inner diameter portion 19 of the catheter unit luer inlet taper extension through the main body of the catheter unit and out the small outlet taper extension 18 through flexible tube (cannula) 22 which is inserted and left in the patient's vein in the wrist area upon withdrawal of needle 14. At the other end of needle body 13 is a tubular opening where blood egresses on placement of the needle in the patient's vein.

The main body 16 of the catheter unit has a large inlet taper extension 17 whose inner diameter decreases from the inlet to the outlet, viz., small outlet taper extension 18, with the inner diameter of the catheter unit being largest at inner diameter 19 of the large inlet taper extension 17. Located at the outermost portion of large inlet taper extension 17 is flange 20 permitting a cap, e.g., a rubber cap 46 (FIG. 7) to be attached to stop the flow of blood and allow the injection of drugs. Flange 20 preferably is provided with beveled corners 21 which permits closure of the inner diameter with a nut (not shown) normally part of the tubing attaching unit. At the other end of small outlet taper extension 18, there is secured flexible, e.g., Nylon, Teflon, etc., tubing 22, a portion of which is inserted and left in the patient's wrist vein, upon withdrawal of needle 14.

Air can be vented from the feed bottle tube 12 at the inlet end 17 of the catheter unit when valve cap 24 is rotated into the vent or I.V. fluid shutoff position. The position of valve cap 24 in the vent position is illustrated in FIGS. 5 and 6. When liquid egresses through vent hole 23, the applicable medical standard of care has been met and catheter unit operator or technician is reasonably assured that the risk of air embolism is medically acceptably minimal. When fluid has egressed through vent hole 23, the technician rotates valve cap 24 approximately ninety degrees (90°) to the flow position, as shown in FIGS. 3 and 4, allowing fluids to flow into the patient. The valve portion of catheter unit 16 contains valve cap 24 at the top thereof which is secured by screws 29 to upper portion 33 of the rotary valve of the catheter unit. Located internally within upper portion 30 is a molded seat 25 on which rests upper O ring 26. Correspondingly, lower seats 32 are provided on rotary valve 33 for lower O rings 31. Rotary valve 33 is provided with a port or opening 34 to allow communication of flexible tube 22 with the tapered inner diameter of large inlet taper extension 17, thereby allowing flow of I.V. fluids into the patient when valve cap 24 is rotated into the I.V. fluid flow position.

As will be noted from FIG. 3, in the fluid flow position, ball 27 is pressed by Belleville springs to block vent hole 23, prohibiting air or fluids from either entering or exiting from the valve.

Screws 29 pass through openings 61 (see FIG. 2) and are secured to rotary valve 33 in the upper portion thereof through threaded openings 62. Of course, other means can be employed to secure valve cap 24 to the main body of rotary valve 33.

The bottom deck 63 (FIG. 2) of catheter unit main body 16 may be secured to the lower surface of the patient's wrist 11 (FIG. 1) by use of double-sided foam rubber tape 35 which serves as a cushion. Alternatively it can be secured to the back (upper surface) of the patient's hand, his arm, etc. Upper adhesive layer 36 secures the bottom of bottom deck 63 to foam rubber tape 35 which is in turn secured to the patient's wrist by lower adhesive wear 37 upon removal of release layer 39, preferably of Kraft paper. Suture holes 60 are provided in bottom deck 63 to permit more permanent securing of the catheter unit if medically indicated. At one, or both sides thereof, there can be provided one or more integral tube holder clip(s) 39 having a curved receptacle portion 40 to retain I.V. tube(s) 12 therein.

Rotary valve cap 24 has ears 43 (FIGS. 4 and 6) by which it can be rotated to the I.V. liquid flow and air/blood vent positions, respectively. Stop means, e.g., pin 41, engages the inner aspects of ears 43 to serve to lock valve cap 24 in the respective fluid flow and vent positions. Detents 42 restrict the motion of ears 43 on valve cap 24.

Ferrules 44 (preferably glass-epoxy) are used to join flexible tube (cannula) 22 to the small outlet taper extension 18, as shown in FIGS. 3 and 5. On the other end of the catheter unit in the position of large inlet taper extension 17, ferrule 45 (preferably of glass-epoxy) is used to bond needle or stylet 14 to the needle body 13 (FIGS. 3 and 5).

It will be observed that FIGS. 3 and 5 are approximately 90° apart with respect to the position of rotary valve 33 and valve cap 24. As is shown in FIG. 7, push valve cap 46 can be employed as a closure means when attached to flange 20, e.g., during periods when the catheter is not in active use.

Figure 8:
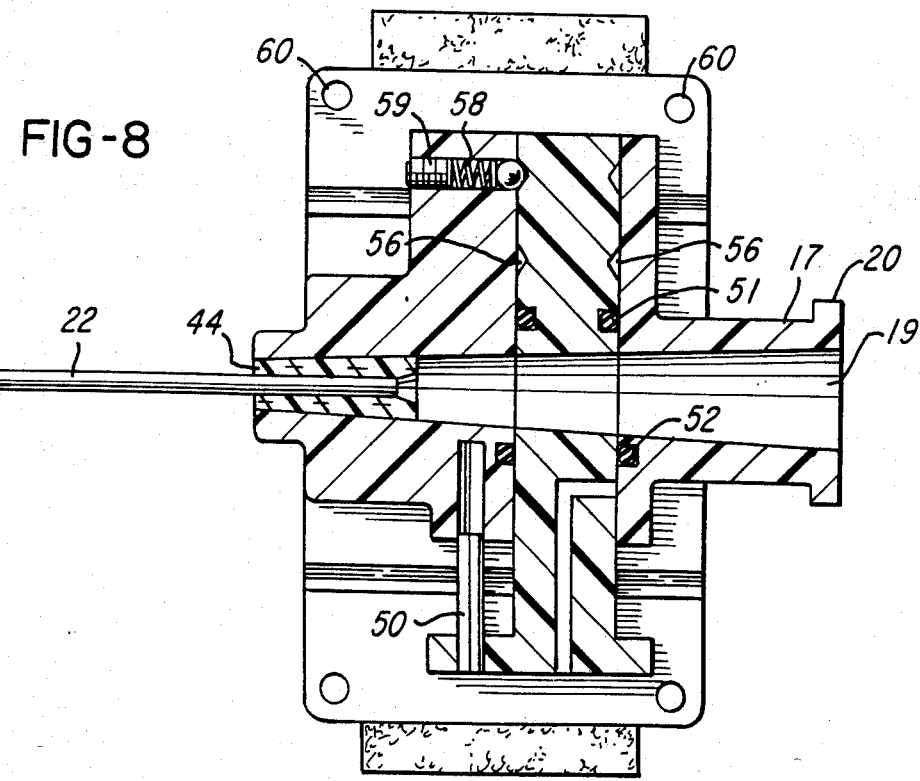
FIG. 8 is a top plan view with parts broken away and parts in section illustrating a modification of the catheter unit of FIG. 2 with means for mounting the flow/venting valve means on the side rather than on the top of said unit.

FIGS. 8 and 9 show alternate modifications, respectively, having means for mounting the rotary valve on the side of the catheter unit rather than on the top thereof as is shown in FIGS. 1 through 6. As is shown in FIGS. 8 and 9, vent hole or passageway 48 is provided in valve rod 54 so that pressure on push valve cap 47 permits passageway 48 to travel so as to be placed in position in line with inner diameter 19, thereby permitting the venting of air as necessarily and desirably occurs when changing I.V. bottles. When liquid is observed to exit through vent hole/passageway 48, drug flow can be resumed and venting has been completed. Coil (compression) spring 49 otherwise maintains passageway 48 in a non-communicating relationship with the inner diameter 19, viz., in the fluid flow position, as shown in FIG. 8. Guide pin 50 keeps push valve cap 47 in proper alignment to permit venting of the catheter unit having the side vented valve in the manner described above. Ball and compression spring arrangement 58 engage keeper notches 56 in valve rod 54 in the embodiment of FIG. 9. Set screw 59 can be adjusted to vary the force of engagement between arrangement 58 and notches 56. In the embodiment of FIG. 9, push valve cap 47 is pushed to align passageway 48 with opening 19 until desired venting occurs. Push valve cap 47 and valve rod 54 are positionable in two positions: an IV flow position, shown in FIG. 9, and a vent position (not shown) where ball 58 engages the second of notches 56 of FIG. 9.

The embodiments of FIGS. 8 and 9 are provided with a smaller "O" ring 51 and larger "O" ring 52 to serve as gaskets much in the same manner as "O" rings 26 and 31, respectively, of FIGS. 3 and 5. In the embodiments of FIGS. 3 and 5, however, lower "O" rings 31 are the smaller ones whereas upper "O" rings 26 are larger.

Valve rod 54 has a threaded portion 53 which is secured by locknut 55 in the FIG. 8 modification. In the FIG. 9 modification, detents 56 serve as temporary seats for the engaging portion of ball 57, backed up by spring 58, which is maintained at the desired tension by means of set screw.

In application the technician removes the unit from a sterile, bubble-pack type, container, removes the Kraft-type protective paper on the sticky tape, removes the protective cap covering the needle/cannula and inserts same into the patient's vein. At this time the rotary valve cap (43) is in the "flow" position allowing the needle to be used for puncture. After puncture, the needle is removed allowing the option of two procedures, i.e.:

(1) Place a rubber cap over the flange (20) to allow needle insertion of fluids. To do this, rotate the rotary valve cap to "vent." This stops the flow of blood while installing the rubber cap (46). Rotating the valve cap (24) slowly between flow and vent will cause the blood to escape through the vent hole, forcing air ahead of it.

(2) The internal luer taper (19) allows the tapered end of the I.V. tubing to be coupled, again after needle removal. Rotate the rotary valve cap (24) to the vent position and couple the tubing. By releasing a tube clamp (not shown) on the tubing, the fluids are allowed to flow into the body of the catheter and out the vent hole forcing air ahead of it. Upon seeing the fluids escaping the vent hole, rotate the rotary valve cap (24) back to the flow position. This couples the fluids to the vein with considerably less possibility of air entrapment.

It will be observed that there has been described a winged catheter unit having provided therein means to vent air/blood/fluids and alternatively permit the safe passage of I.V. fluids through a patient's veins. The I.V. winged catheter unit does not require removal and permits a very safe mode of operation when initiating and changing bottles of intravenous fluids being administered to a patient.

It will be observed that while the foregoing description has been applied to use of the catheter unit of the present invention for patients who are being transported in emergency vehicles to a hospital, it should be observed that the catheter unit of this invention is equally applicable for use on stable patients, viz., those already in hospital beds inasmuch as many of the same problems are presented to health care providers in a hospital, such as doctors, nurses, etc., as are faced by paramedics and similar ambulance technicians during the transport of patients.

What is claimed is:

1. A winged catheter unit capable of being temporarily attached to a patient at a point near where an intravenous catheter injection tube is to be inserted into the patient, comprising:
   a catheter main body having a lower portion adapted to connect in facial contact to a patient's body;
   a fluid flow conduit means connected to said main body having an internal passageway for the passage of intravenously injected medicaments and/or the backflow of blood from said patient, said conduit means having an inlet end and an outlet end;
   cannula means connectable between the outlet end of said conduit means and the interior of a blood vessel;
   valve means interposed within and transversely to said conduit means operably positionable between an open and a closed position, said inlet end of said conduit means being fluidly connected to said cannula means when said valve is in said open position;
   vent means for releasing air from said cannula and conduit means when said valve means is in the closed position to avoid introducing an air embolus into said blood vessel.

2. A winged catheter unit as in claim 1 wherein said valve is a rotary valve.

3. A winged catheter unit as in claim 1 wherein said valve is a slide valve.

4. A winged catheter unit as in claim 1 which includes openings in said molded deck unit for suturing said winged catheter unit to a patient.

5. A winged catheter unit as in claim 1 wherein said larger inner diameter inlet extension portion of said tapered tubular portion has an integral flange on which said catheter inlet closure means is located.

6. A winged catheter unit as in claim 3 wherein said slide valve is a spring-biased side mounted push valve.

7. A winged catheter unit as in claim 2 wherein said means to position said rotary valve between air venting and fluid flow positions has a top mounted valve cap having ears, the inner aspects of which engage a stop means to lock said valve cap in its respective vent and flow positions.

8. The winged catheter unit of claim 1, including adhesive means for releasably connecting the unit to a patient.

9. The winged catheter unit of claim 1, wherein said valve means is positioned transversely to the elongate axis of the conduit means.

10. A method for venting the winged catheter unit of claim 1 of any air embolisms before intravenously introducing fluid to a blood vessel, comprising the steps of:
   (a) connecting the unit to a patient near a point wherein fluid is to be introduced to the patient;
   (b) inserting a needle means through said passageway, through said cannula, through the patient's skin and into a blood vessel;
   (c) thereafter inserting said cannula into said blood vessel;
   (d) withdrawing said needle from said unit;
   (e) positioning said valve means to the closed position;
   (f) connecting a fluid supply to the inlet end of said unit;
   (g) waiting until fluid emerges from said vent means;
   (h) positioning said valve means in the open position for flow into the patient.

* * * * *